United States Patent
Yang

(10) Patent No.: US 6,283,116 B1
(45) Date of Patent: Sep. 4, 2001

(54) TRIGGER FOR A PORTABLE HEAT PACK

(76) Inventor: Yong Sung Yang, 419-25, Sungnae-Dong, Kang Dong-Ku, Seoul (KR)

( * ) Notice: Subject to any disclaimer, the term of this patent is extended or adjusted under 35 U.S.C. 154(b) by 0 days.

(21) Appl. No.: 09/502,545

(22) Filed: Feb. 10, 2000

(51) Int. Cl.[7] .................................................... F24J 1/00
(52) U.S. Cl. ............................. 126/263.03; 126/263.01; 422/245.1
(58) Field of Search .............................. 126/204, 263.03, 126/263.04; 252/70; 422/245.1; 44/250; 607/114

(56) References Cited

U.S. PATENT DOCUMENTS

| | | | |
|---|---|---|---|
| 708,549 | * | 9/1902 | Heiliger ........................ 126/263.04 |
| 2,220,777 | * | 11/1940 | Othmer ......................... 126/263.04 |
| 4,379,448 | * | 4/1983 | Kapralis et al. .............. 126/263.04 |
| 4,460,546 | * | 7/1984 | Kapralis et al. .............. 126/263.04 |
| 4,572,158 | | 2/1986 | Fiedler . |
| 4,872,442 | * | 10/1989 | Manker ......................... 126/263.04 |
| 4,899,727 | | 2/1990 | Kapralis et al. . |
| 5,205,278 | | 4/1993 | Wang . |
| 5,736,110 | * | 4/1998 | Angelillo et al. ............ 126/263.04 |
| 5,805,766 | * | 9/1998 | Wang ............................. 126/263.01 |

* cited by examiner

*Primary Examiner*—James C. Yeung
(74) *Attorney, Agent, or Firm*—Christie, Parker & Hale, LLP

(57) ABSTRACT

A triggering element for a portable heat pack having a sealed bag capable of transferring heat and a sodium acetate solution that generate a crystallization heat contained in said sealed bag. The triggering element comprises a thin, flexible strip of stainless steel; the strip having an oval shape with the length and a center portion formed in a bowl-shaped configuration with one surface depressed inward to form a concave shape surface and the convex surface opposite side with a protruded surface, and the depth of the center portion depressed inward. The strip has an the outer annular portion and a plurality of slits cut through said center portion.

2 Claims, 2 Drawing Sheets

Fig. 1
_PRIOR ART_
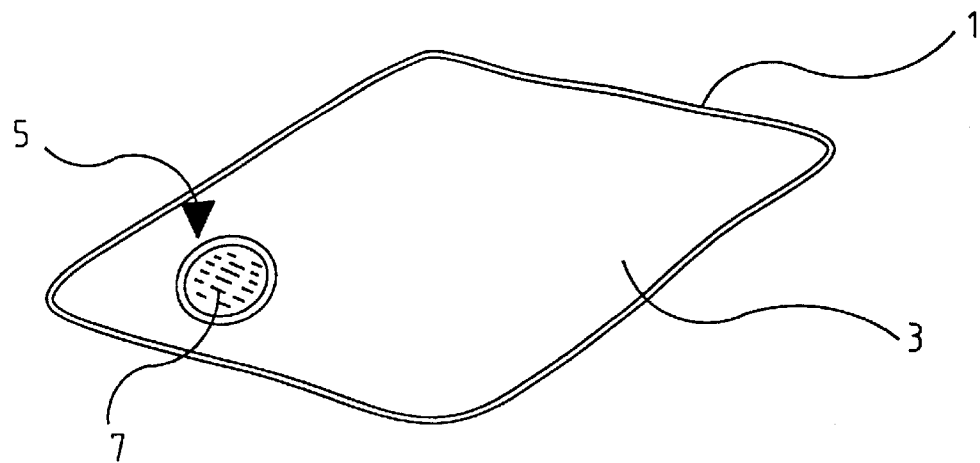

TRIGGER FOR A PORTABLE HEAT PACK

BACKGROUND OF THE INVENTION

The present invention relates to a triggering element for a portable heat pack, more particularly, a trigger element which generates an oscillation wave initiate a crystallization heat contained in a sealed bag.

Referring to FIG. 1, a conventional portable chemical bag warmer comprises a sodium acetate solution 3, which generates a crystallization heat, contained in a sealed bag 1. A trigger is typically formed in a thin disc-shape made of a metal piece and placed in the inside of the sealed bag in a non-fixed manner. The trigger has a plurality of slits which initiate an oscillation wave when the edges that form the slits make contact creating friction.

The liquid sodium acetate solution 3 is initiated to start crystallization to generate heat when triggering member is pressed down and up causing edges of the slits 7 to make contact creating a friction, thereby an oscillation wave is generated. However, if the initial triggering action fails to create the oscillation wave, then the user must repeat the pressing process in attempt to generate the oscillation wave which is inconvenient for the user to operate.

U.S. Pat. No. 5,205,278 utilizes a disc-shaped element made of a flexible metal with a center portion divided into four sectors to direct the vibration to four directions as a trigging member. However, since the surface of the trigging member dose not automatically restore back to the original shape and if the oscillation wave is not generated in the first attempt, the user must manually return the triggering member to the original state in order to make a second attempt to generate the oscillation wave.

Still, U.S. Pat. Nos. 4,899,727 and 4,572,158 disclose triggering members having different formation of the slits and the edges that form the slits in effort improve the reaction effect in initiating crystallization of the sodium acetate solution. However, both inventions failed to provide the triggering member which automatically returns to the original configuration after a snap-action causing the trigger member to deform.

SUMMARY OF THE INVENTION

It is a primary object of this invention is to the overcome the disadvantages of the prior art by providing a heat pack which a user can conveniently utilize.

The foregoing object is satisfied by a triggering element for a portable heat pack having a sealed bag capable of transferring heat and a sodium acetate solution that generate a crystallization heat contained in the sealed bag. The triggering element characterized as comprising a thin, flexible strip of stainless steel; having an oval shape and a center portion formed in a bowl-shaped configuration with one surface depressed inward to form a concave shape surface and the convex opposite side surface having protruded surface. The center portion depressed inward has an outer annular portion with a plurality of slits cut through the center portion.

BRIEF DESCRIPTION OF THE DRAWINGS

FIG. 1 is a perspective view of a conventional heat pack.

DETAILED DESCRIPTION OF THE INVENTION

A heat pack generally consists a sodium acetate solution contained in a sealed pack made of PVC, P.P. or P.U. material to generate a crystallization heat activated by an oscillation wave.

A triggering element which initiates the oscillation wave is placed in the inside of the sealed pack and floats around freely. The triggering element 15 in accordance with the present invention is made out of a thin, flexible stainless steel strip. The triggering element 15 has a center portion 18 having one surface depressed inward to form a concave shape surface and the opposite side is a convex surface with protruded surface such that a snap-action is possible when the convex surface is pushed down, and outer annular portion 19. Moreover, a plurality of slits are cut through the center portion 18 of the triggering element 15 such that when the cut opposed edges of the slits 17 make contact, friction is generated to create the oscillation wave. The triggering element 15 is formed in an oval shape in which one side is longer than other side so that the when a pressure applied causing the trigger element to bend is released, the trigger element automatically returns to a stable configuration.

Figure 2:
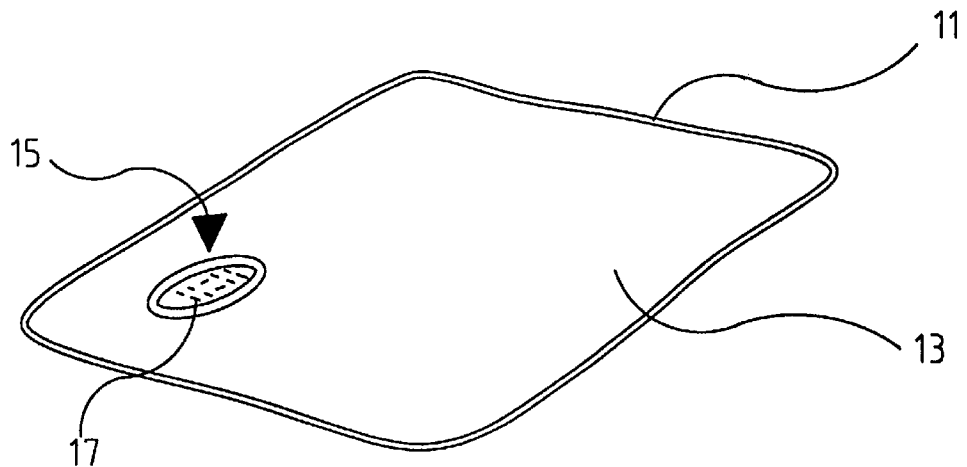
FIG. 2 is a perspective view of a first embodiment according to the present invention.

FIG. 2 illustrates a portable heat pack employing a triggering element according to the present invention. A portable heat pack comprises: a sealed bag 11 capable of transferring heat: a sodium acetate solution 3 that generate a crystallization heat contained in the sealed bag; a triggering element formed with a thin, flexible stainless steel and placed in the inside of the sealed bag in a non-fixed manner to allow it move around freely; and a plurality of slits 17 formed on the surface of the triggering element 15 so that when the edges of the slits make contact, friction is generated to create the oscillation wave.

Figure 3:
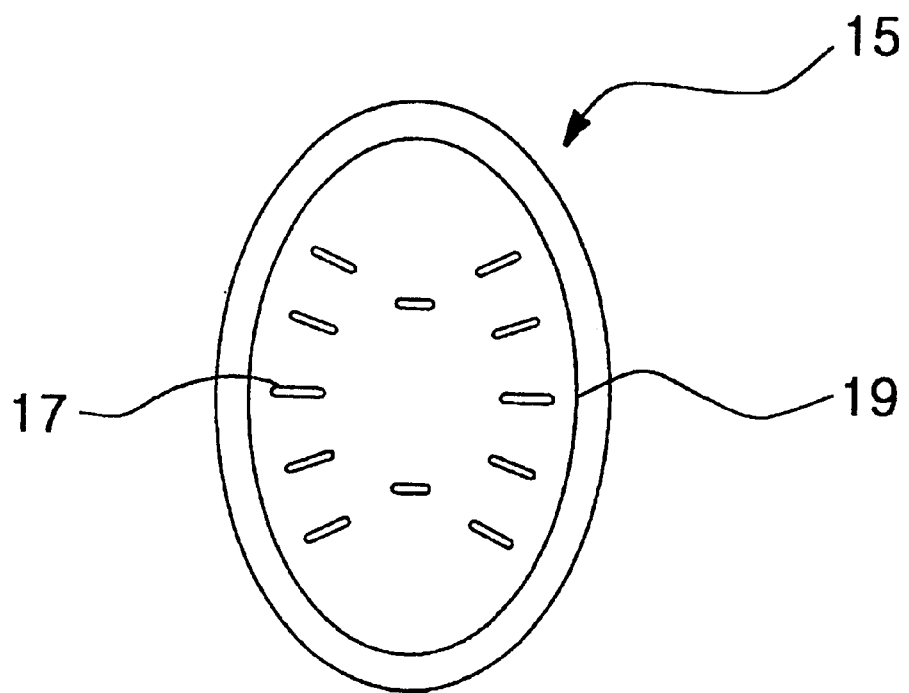
FIG. 3 is a top plan view of triggering element of FIG. 2.
Figure 4:
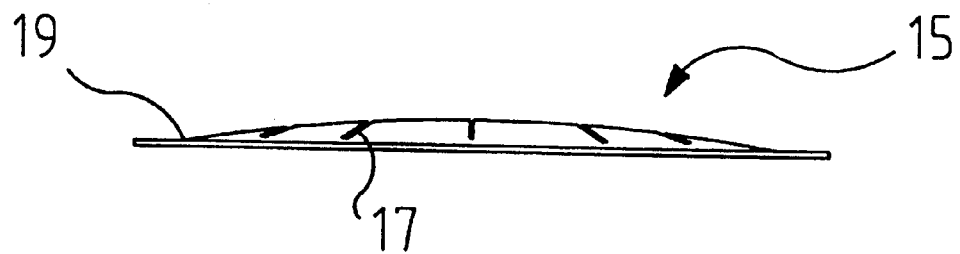
FIG. 4 is a side elevational view of the triggering element of FIG. 3.

The important feature of the present invention is the shape of the triggering element. FIG. 3 and 4 illustrate a triggering element according to the first embodiment of the present invention. The triggering element 15 is made out of stainless steel in an oval shape. The ratio of the longish length (a) and the width (b) of the oval. The triggering element 15 has a center portion 18 formed in a bowl-shaped configuration having one surface depressed inward to form a concave shape surface and the convex surface opposite side with protruded surface, and the outer annular portion 19. The depth (c) of the center portion 18 depressed inward. It is preferable to place a plurality of slits 17 as illustrated in FIG. 3 to maximize the reaction effect, although other placements may be possible.

The operation of the triggering element for heat pack according to the present invention is described hereinafter.

The heat pack consists with a sodium acetate solution 13 in a liquid form and a triggering element 15 which initiates the oscillation wave to begin crystallization of the sodium acetate solution 13. The triggering element 15 according to the present invention is formed in an oval shape with the center portion 18 depressed inward. This particular construction of the triggering element provides the automatic restoration process in which the triggering element returns to its original shape when pressure is released. As a result, a user only needs to apply a pressure to the triggering element once to have two attempts at generating the oscillation wave to deliver energy to the sodium acetate solution 13 since the second attempt is automatically made as the trigger automatically restore back to its stable configuration upon release of the pressure. The oscillation wave initiates the sodium acetate solution 13 to start a crystallization reaction which generates heat.

After the sodium acetate solution has been completely crystallized causing generation of heat in the heat pack, the heat pack my be reused by converting the solid crystalline sodium acetate back to a liquid form by placing the heat pack in a boiling water for a fixed period of time.

Since the triggering element according to the present invention provides automatic restoration process in which the user only needs to apply a pressure to the triggering element once to have two attempts at generating the oscillation wave, it is much more convenient than the conventional trigger for the heat pack.

It is understood that the foregoing detailed description is given merely by way of illustration and that many variations may be made therein without departing from the spirit of this invention.

What is claimed is:

1. A triggering element for a portable heat pack having a sealed bag capable of transferring heat and a sodium acetate solution that generates a crystallization heat contained in said sealed bag, said triggering element comprising:

(a) a thin, flexible strip of stainless steel;

(b) said strip having an oval shape;

(c) said strip having a center portion formed in a bowl-shaped configuration in which one surface is depressable inward to form a concave shape surface and the opposite side to form a convex surface with a protruded surface;

(d) said strip having an outer annular portion; and (e) said strip having a plurality of slits cut through said center portion;

(f) said triggering element automatically returning to the original configuration upon release of pressure thereon.

2. A triggering element according to claim 1 wherein said triggering element has a shape in which one side is longer than the other side so that when pressure is applied the triggering element is caused to bend, and then automatically returns to a stable configuration.

* * * * *